(12) United States Patent
Karmali

(10) Patent No.: US 7,601,834 B2
(45) Date of Patent: *Oct. 13, 2009

(54) COMPOSITIONS AND METHODS OF REDUCING SIDE EFFECTS AND TOXICITY OF METHOTREXATE WHEN GIVEN AS OROTATE DERIVATIVES

(75) Inventor: Rashida A. Karmali, Brooklyn, NY (US)

(73) Assignee: SavviPharm Inc, New York, NY (US)

( * ) Notice: Subject to any disclaimer, the term of this patent is extended or adjusted under 35 U.S.C. 154(b) by 183 days.

This patent is subject to a terminal disclaimer.

(21) Appl. No.: 11/655,801

(22) Filed: Jan. 18, 2007

(65) Prior Publication Data

US 2007/0179145 A1    Aug. 2, 2007

Related U.S. Application Data

(63) Continuation-in-part of application No. 11/063,943, filed on Feb. 22, 2005.

(51) Int. Cl.
*C07D 475/08* (2006.01)
*A61K 31/519* (2006.01)

(52) U.S. Cl. .................. 544/260; 514/262.1
(58) Field of Classification Search ......... 514/262.1; 544/260
See application file for complete search history.

(56) References Cited

U.S. PATENT DOCUMENTS

| | | | |
|---|---|---|---|
| 5,698,556 A | 12/1997 | Chan | 514/249 |
| 5,728,707 A * | 3/1998 | Wehrmann | 514/274 |
| 5,861,406 A * | 1/1999 | Wehrmann | 514/274 |
| 5,912,346 A * | 6/1999 | Wehrmann | 544/310 |
| 5,958,928 A | 9/1999 | Mihara | 514/258 |
| 6,184,227 B1 * | 2/2001 | Karmali | 514/274 |
| 6,559,149 B1 | 5/2003 | Matsuoka | 514/249 |

OTHER PUBLICATIONS

Gould, P.L. International Journal of Pharmaceutics, 1986, vol. 33, pp. 201-217.*

* cited by examiner

*Primary Examiner*—Ardin Marschel
*Assistant Examiner*—James D Anderson
(74) *Attorney, Agent, or Firm*—Rashida A. Karmali

(57) ABSTRACT

This invention is in the field of chemical restructuring of antimetabolite agents known to have poor oral bioavailability and to cause tissue toxicity as a side effect, by producing their orotate derivatives. More particularly, it concerns orotate derivatives of the methotrexate and trimetrexate, that are found to improve the oral bioavailability and clearance compared with their respective forms—methotrexate and trimetrexate, currently in use. The present invention provides methotrexate orotate having the formula:

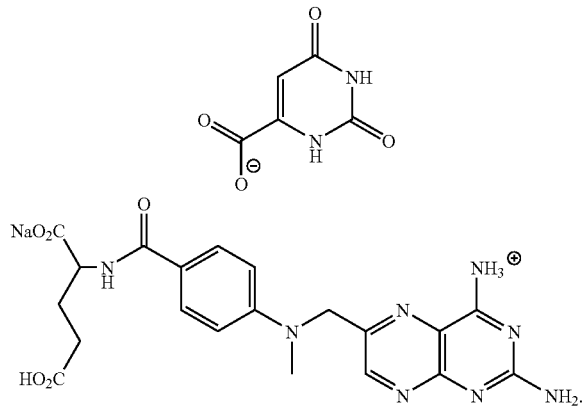

2 Claims, 5 Drawing Sheets

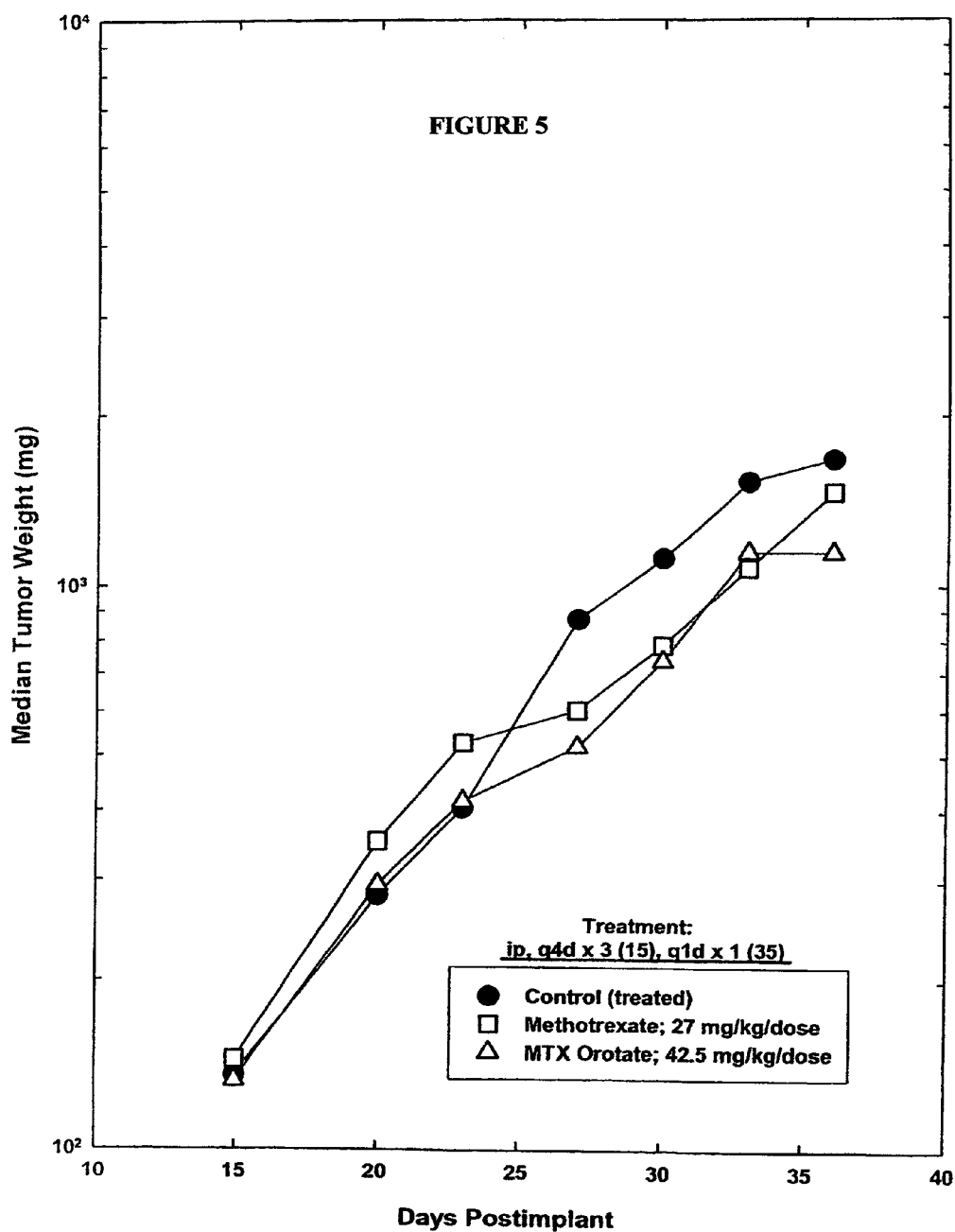

COMPOSITIONS AND METHODS OF REDUCING SIDE EFFECTS AND TOXICITY OF METHOTREXATE WHEN GIVEN AS OROTATE DERIVATIVES

CROSS-REFERENCE TO OTHER APPLICATION

This application is a Continuation-in-part of U.S. patent application Ser. No. 11/063,943 filed Feb. 22, 2005, which is incorporated herein, with references in its entirety.

1. FIELD OF INVENTION

This invention is related to orotic acid derivatives of pharmaceutical agents and in particular to the conversion of methotrexate to their orotate derivatives to improve bioavailability and drug clearance thereby reducing toxicity in cancer patients and in non-infectious, non-neoplastic inflammatory conditions such as rheumatoid arthritis, psoriasis, systemic lupus, and multiple sclerosis.

2. BACKGROUND TO THE INVENTION

This invention is in the field of chemical restructuring of methotrexate and related pharmaceutical agents known to have poor bioavailability, cause toxicity or adverse drug reactions in noncancerous tissues as a side effect, by producing their orotate derivatives. More particularly, it concerns derivatives of the folate antagonists, methotrexate, trimetrexate and raltitrexed that are used as anticancer drugs on in non-malignant disorders characterized by rapid cellular growth.

In the 58 years since Farber first described clinical remissions after use of the folate antagonist aminopterin for children with acute leukemia, methotrexate has been used to treat millions of patients with both malignant and autoimmune diseases. Methotrexate is now the most widely prescribed disease-modifying antirheumatic drug (DMARD), used by at least 500,000 patients worldwide with rheumatoid arthritis. Methotrexate is prescribed for more patients with rheumatoid arthritis than all of the biologic drugs in current use combined. It is the most commonly reported agent used in combination with other DMARDs where clear additive therapeutic value is demonstrated. Low doses of methotrexate administered orally, have been iused in treatment of multiple sclerosis with minimal toxicity. However, when administered orally the serum level of methotrexate is not sufficient because of poor oral bioavailability. The fear of severe organ-associated toxicity has led to development of guidelines for monitoring liver toxicity which has so frightened physicians and limited its earlier use. In addition, the recognition that methotrexate-associated pulmonary disease is most often a subacute syndrome associated with dry cough, often with dyspnea and fever, has led to earlier recognition and avoidance of permanent lung sequelae in many patients receiving the drug. The realization that many of the gastrointenstinal, bone marrow and other toxicities, which so frequently limited its use prior to 1980s could be avoided by the use of folate supplementation has also given both clinicians and patients a measure of security when prescribing this potent antimetabolite.

However, the overall sophistication regarding the many issues and complexities associated with the use of methotrexate is still somewhat low. Many clinicians use folic acid, while others use methotrexate with a variety of other drugs in patients who may be at increased risk of adverse events due to drug interactions. Ideas and prescribing patterns associated with maximum weekly doses, use in the elderly, monitoring of blood tests, and when to "give up" and add other agents to be prescribed with methotrexate are often followed without specific rigorous scientific support.

The Food and Drug Administration approved low-dose methotrexate use in treatment of psoriasis in 1960 and in the treatment of rheumatoid arthritis in 1988. Currently, methotrexate is prescribed by rheumatologists world-wide and has proved to be a very effective, fast-working, second-line antirheumatic agent with the best efficacy-toxicity ratio. Nevertheless, the main reason for discontinuation of methotrexate is not inefficacy but toxicity. Because of its clear-cut and long-lasting efficacy, much effort is currently being made to develop strategies to decrease or prevent its toxicity. In approximately 30% of rheumatoid arthritis patients, toxicity leads to discontinuation of methotrexate therapy. Therefore, the present invention provides two solutions to diminishing the toxicity of methotrexate: 1) by improving the bioavailability of methotrexate and therefore reducing the effective dose of methotrexate, and 2) by improving the clearance rate of methotrexate.

Side Effects—The side effects of methotrexate are quite common. The severity varies, but most side effects are mild, reversible, and can be treated conservatively. Side effects like nausea, changes in transaminases, and somatitis are often encountered and are dose dependent; others like pneumonitis and hepatocellular changes are not. However, on 30% of patients with rheumatoid arthirits, toxicity leads to discontinuation of methotrexate therapy within one year. Only a few determinants for toxicity are known, such as increasing age and poor renal function. Another important problem is that although the risk of side effects may be slightly higher in the first six months, the risk for all sorts of adverse effects is permanent, implying a need for long-term monitoring. At least part of the side effects of methotrexate seems to be directly related to its folate antagonism and its cytostatic effects especially in tissues with high turnover. Methotrexate is prescribed in a dose of 5 mg/week to 15 mg/week and the maximum dose is 25 to 30 mg/week. Reduced bioavailability of methotrexate accounts for these effects. Therefore, the present invention provides strategies to improve the bioavailability of methotrexate by converting it to an orotate form and thus reduce its toxicity.

Because of the value of methotrexate in therapy, many investigators have modified the structure of methotrexate in attempts to synthesize more potent derivatives. U.S. Pat. No. 5,698,556, issued to Carcy L. Chan, and U.S. Pat. No. 5,958, 928, issued to Masahiko Mihara. Methotrexate enters cells via the reduced folate carrier which also transports the naturally occurring reduced folates. Efflux of methotrexate occurs through mechanisms that are somewhat different from influx and are energy-dependent. Multi-drug resistance-associated proteins have been identified which transport methotrexate, folic acid and 5-CHO—FH4 out of cells. Inhibition of the multi drug resistance proteins results in significant accumulation of intracellular methotrexate. The present invention provides strategies to improve the efflux and clearance of methotrexate by converting it to an orotate form and improving its clearance. More effective and less toxic agents are widely sought and are a fundamental object of the invention. The pertinent subject matter of the above references is specifically incorporated herein by reference.

3. SUMMARY OF THE INVENTION

The present invention seeks to overcome drawbacks inherent in the prior art by providing compositions of orotate derivatives of methotrexate or trimetrexate that display increased bioavailability and renal clearance when compared with non-derivatized forms of pharmaceutical agent.

This invention is in the field of chemical restructuring of current pharmaceutical agents in use, known to cause tissue toxicity as a side effect, by producing their orotate derivatives. More particularly, it concerns orotate derivatives of the methotrexate, that is used as an anticancer or a disease modifying antirheumatic drug.

In view of the foregoing state of the art, the inventor has designed orotate derivatives of folate antagonists, as exemplified by methotrexate orotate and trimetrexate orotate, containing therein a chemical organic moiety that increases their bioavailability and renal clearance.

The invention also specifically provides a process for the preparation of methotrexate orotate and related derivatives starting from methotrexate, orotic acid and sodium hydroxide hydroxide (or any other alkali such as potassium hydroxide, or aluminium hydroxide). This process comprises a) reacting sodium hydroxide with orotic acid, extracting the sodium orotate, and reacting the sodium orotate extracted with methotrexate to form sodium methotrexate orotate.

Another objective of the invention is to increase the bioavailability of methotrexate when given as methotrexate orotate in human and other mammals.

Yet another objective of the invention is to reduce multidrug resistance when methotrexate is administered in the orotate form.

The invention can also be used to reduce toxicity of methotrexate and trimetrexate when administered as orotate salts.

The invention can also be used to improve the clearance of methotrexate or trimetrexate during first pass when administered as orotate salts through the organs of extraction.

The invention can further be used to reduce drug interactions and side effects when the methotrexate or trimetrexate are administered as orotate salts.

Another objective of the invention is to provide compositions for treating human neoplasms, and particularly, primary or metastatic tumors, proliferative hematopoietic disorders and leukemias with sodium methotrexate orotate and reducing the toxic secondary effects of the drug by reducing the levels of the drug in noncancerous tissues that are susceptible targets of drug toxicity, by 10% to 100% when compared with giving methotrexate.

A preferred embodiment of the invention comprises compositions of methotrexate orotate for treatment of anti-inflammatory diseases comprising rheumatoid arthritis, psoriasis, multiple sclerosis and others.

4. BRIEF DESCRIPTION OF FIGURES

Figure 3:
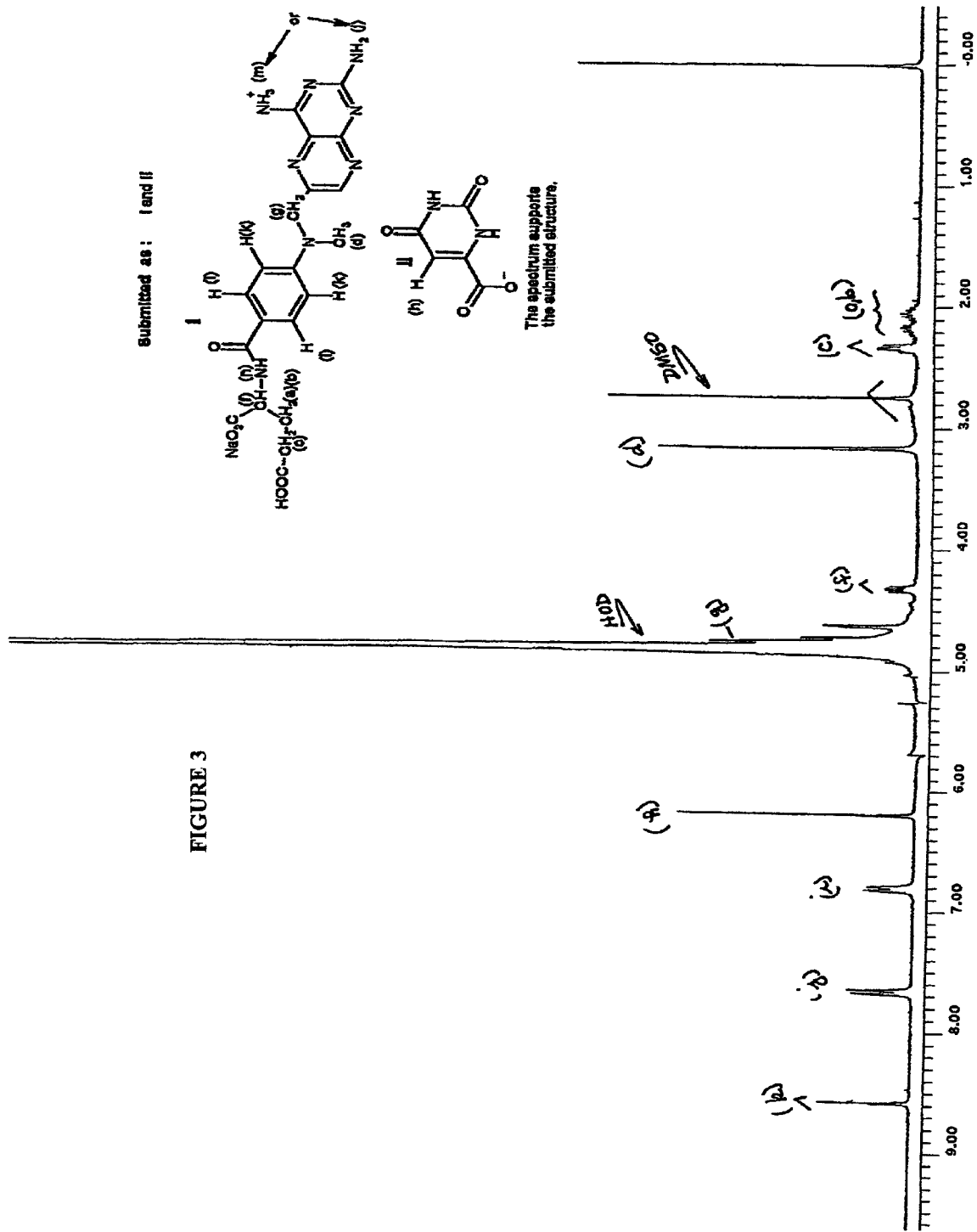

FIG. 3 Mass Spectrograph illustrating methotrexate orotate

Figure 4:
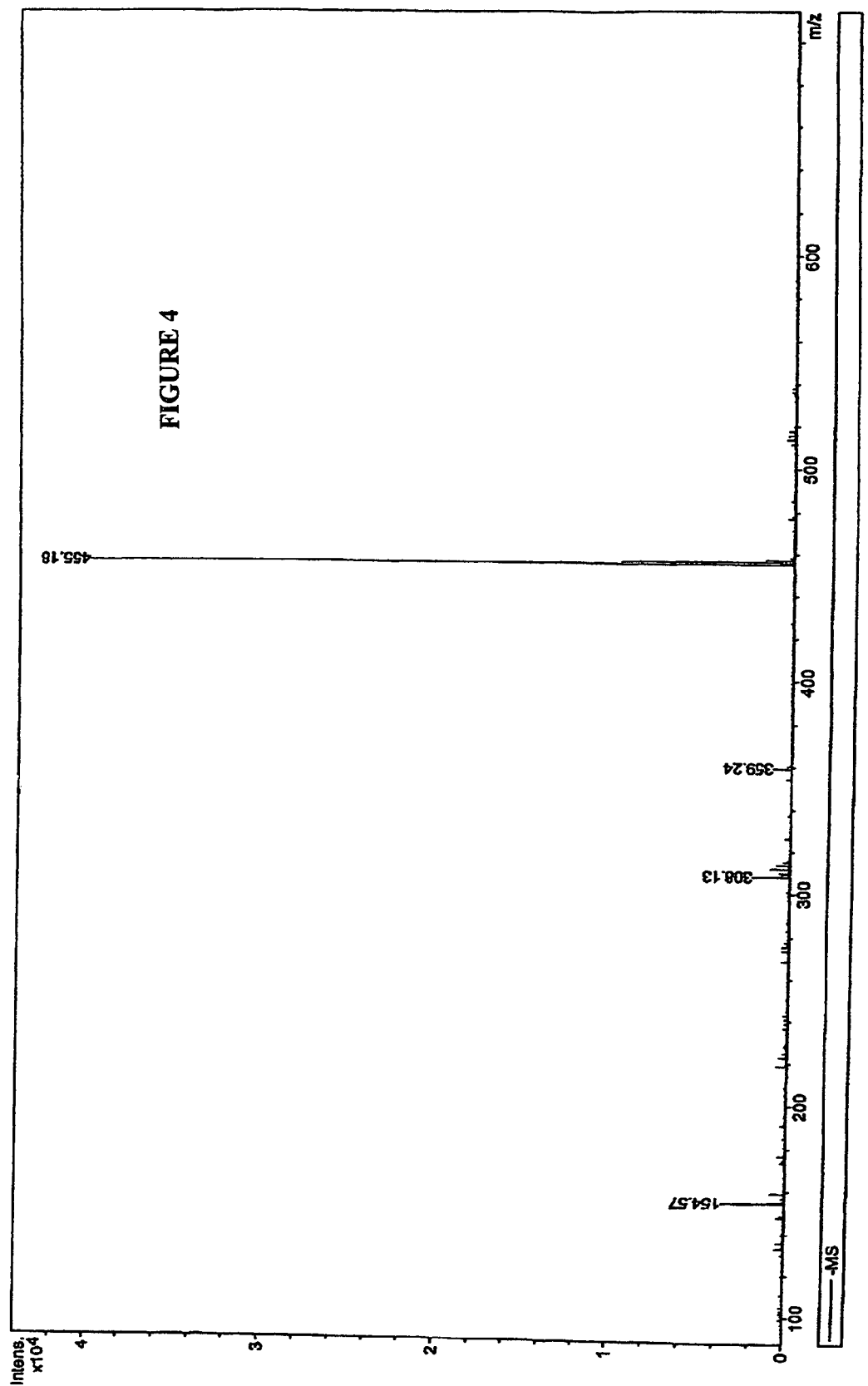

FIG. 4 NMR illustrating methotrexate orotate

FIG. 5 illustrates the response of SC Du-145 Prostate Tumor to treatment with methotrexate or methotrexate orotate.

5. DETAILED DESCRIPTION OF THE INVENTION

Drug therapies that are used for the treatment of patients with cancer can damage a number of organs and organ systems. Among those most frequently damaged are tissues with rapid cell turnover, such as the hematopoetic system, the gastrointestinal tract, and the genitourinary tract. Some drugs are toxic by themselves, but their toxicity may be potentiated when they are used in combination with other agents, the combination may be more toxic than the sum of the toxicities of the individual components. As it is necessary to achieve the greatest antitumor potential of the drug while keeping end-organ toxicity at an acceptable level, the evaluation of patients treated with toxic drugs must be individualized.

It is an objective of the present invention to reduce the magnitude and occurrence of that initial liver insult caused by the drug, by reducing the levels of the drug in the liver by preventing accumulation and/or ensuring faster of the drug from the liver tissue when chemotherapy is administered thereby reducing the release of free radicals.

At most pharmaceutical companies, while many technologies such as combinatorial chemistry, nanotechnology, rapid analog synthesis, automated synthesis open access liquid chromatography mass spectrometry, and high-speed automated high-performance liquid chromatography are now affecting medicinal chemistry, their main effect has been to shorten the cycle time of synthetic operations. One of the most difficult properties to build into a newly discovered lead molecule is the desired pharmacokinetic profile, particularly in the case of orally dosed compounds. "Most experienced medicinal chemists would prefer to start in a structural series that has inherently good pharmacokinetic properties, albeit with poor potency on the target receptor, and then set about improving the potency on the target, rather than working in the other direction", "Organic Chemistry in Drug Discovery, Drug Discovery", Science 303: 1810-1813 (2004).

Improving the Oral Bioavailability of Methotrexate using it in Orotate Form.

The present invention relates generally to the method of increasing the oral bioavailability of pharmaceutical agents that are poorly absorbed from the gastrointestinal tract, and to methods of improved treatment of patients through the oral administration of such agents. In particular, the invention relates to poorly absorbed methotrexate or trimetrexate and converting them to orotate salts to enhance the drugs' oral bioavailability. Thus, the orotate salts of the drugs can be dosed at lower doses to provide the efficacy benefits of a higher dose, while reducing the drugs' toxic effects at lower doses. Additionally, the orotate salts of the pharmaceutical agents have better clearance, that is, the fraction of the drug escaping first pass metabolism is increased, thus reducing the potential for hepatic toxicity. Therefore, an especially useful formulation of the orotate salt of the pharmaceutical agent can provide rapid onset and consistent action using a lower dose and reduce drug interactions and side-effects because of consistent delivery. The present invention provides methods to synthesize orotate salts of water-insoluble drugs having an ionizable center, to improve the drugs' oral bioavailability and efficacy.

The absorption of drugs via the oral route is a subject of intense investigation in the pharmaceutical industry since good bioavailability implies that the drug is able to reach the systemic circulation by mouth. Oral absorption is affected by both the drug properties and the physiology of the gastrointestinal tract, including drug dissolution from the dosage form, the manner in which the drug interacts with the aqueous environment and membrane, permeation across the membrane, and irreversible removal by first-pass organs such as the intestine, liver and lung. Some pharmaceutical agents that exhibit low-solubility show poor bioavailability or irregular absorption, the degree of irregularity being affected by factors such as dose level, fed state of the patient, and physicochemical properties of the drug.

The majority of drug absorption occurs at the small intestine because of the large surface area since the presence of the villi and microvilli increases the absorptive area manifold. The duodenum and jejunum possess the greatest surface areas due to the highest concentration of villi and microvilli in these regions compared with that of the ileum. The circulation of the intestine is unique in that the intestine is the anterior or portal tissue that regulates the flow of substrates to the liver. The intestinal venous blood constitutes about 75% of the blood supply to the liver. Therefore, for drugs that are highly cleared by the intestine, the contribution of the liver, kidney or lung to drug metabolism will become reduced. Conversely, for drugs that are poorly extracted by the intestine, the substrate is able to reach the next organs, the liver and the lung for removal. Therefore, the concentration of drug entering the intestine and the intestinal flow rate alter the rate of drug delivery and affect the rates of intestinal and clearance through hepatic first-pass metabolism.

"Drug bioavailability" is defined here as the amount of drug systemically available over time. The present invention increases drug bioavailability of pharmaceutical agents by converting them into orotate salts. This may be achieved by altering the hydrophilic and lipophilic properties of the drug so that the drug permeates the membrane well and blood perfusion rate becomes the overall rate-limiting step for absorption, or by inhibiting drug biotransformation in the gut and/or by inhibiting active back transport systems in the gut that decrease the net transport of drugs across the gut membrane into the blood stream. In either case, the composition responsible for increased drug bioavailability is the orotate salt of the pharmaceutical agent. For reasons that are not immediately apparent, it has been discovered that conversion of a water-insoluble pharmaceutical agent into an orotate salts provides a method for increasing the bioavailability of an orally administered pharmaceutical agent to a mammal in need of treatment in sufficient amount to provided integrated systemic concentrations over time of the orotate agent over the agent without conversion to an orotate salt.

Changes in the integrated systemic concentrations over-time are indicated by area under the curve (AUC) or $C_{max}$, both parameters well known in the art. AUC is a determination of the Area Under the Curve plotting the serum or plasma concentration of drug along the ordinate (Y-axis) against time along the abscissa (X-axis). Generally, the values for the AUC represent drug concentrations over time in units of mass–time/volume. When efficacy of the orotate salt of the agent is being measured, the amount and form of the active drug administered should be the same in both the administration of the drugs as orotate and the administration of the drug alone.

The present invention provides methods wherein a composition provides an increase in bioavailability of the orotate salt of the pharmaceutical agent as measured by AUC of at least 25% relative to dosing of the pharmaceutical agent. The present invention also provides methods wherein the composition provides an increase in bioavailability of the orotate salt of the pharmaceutical agent as measured by AUC of at least 50% relative to dosing of the pharmaceutical agent. The present invention further provides methods wherein said composition provides an increase in bioavailability of the orotate salt of the pharmaceutical agent as measured by AUC of at least 100% relative to dosing of the pharmaceutical agent.

The invention provides a composition that increases the bioavailability of the orotate salt of the pharmaceutical agent as measured by Cmax of at least 50% relative to dosing of the pharmaceutical agent. The invention also provides said composition that increases the bioavailability of the orotate salt of the pharmaceutical agent as measured by Cmax of at least 100% relative to dosing of the pharmaceutical agent. The invention further provides said composition which provides an increase in bioavailability of the orotate salt of the pharmaceutical agent as measured by Cmax of at least 200% relative to dosing of the pharmaceutical agent. Systemic drug concentrations are measured using standard biochemical drug measurement techniques (Simmons et al., Anal Lett. 39: 2009-2021 (1997).

Characteristics of Drugs Used as Orotate Derivatives

The word "drug" as used herein is defined as a chemical intended for use in the treatment or prevention of disease. Drugs include synthetic and naturally occurring bioaffecting substances as well as recognized pharmaceuticals, such as those listed in "The Physician desk Reference," 56th ed, pages 101-133 (or an updated edition). These references are incorporated by reference herein. The term "drug" also includes compounds that have the indicated properties that are not discovered or available. The present invention can be used with drugs consisting of charged, uncharged, hydrophilic, zwitter-ionic, or hydrophobic species, as well as any combinations of these physical characteristics. A hydrophobic drug is defined as a drug which in its non-ionized form is more soluble in lipid or fat than in water. A preferred class of hydrophobic drugs is those drugs that are more soluble in octanol than in water.

Compounds or drugs from a number of classes of compounds can be converted to orotate derivatives and administered orally as orotate derivatives. The compound or drug can be for example, but is not limited to the following classes: acetanilide, actinomycin D, adriamycin, aminoacridine, aminoimidazole, aminoquinoline, anilide, anthracycline antibiotic, antiestrogen, benzazepine, benzhydryl compound, benzodiazepine, cephalosporine, cisplatin, colchicines, cyclic peptide, cyclophosphamide, daunorubicin, dibenzazepine, digitalis glycoside, dihydropyridine, doxorubicin, epiphodophyllotoxin, epirubicin, ergoline, ergot alkaloid, etoposide, 5-fluorouracil, idarubicin, ifosamide, imidazole, interleukin-2, interferon alpha isoquinoline, macrolide, melphalan, methotrexate, mitomycin-C, mitoxantrone, naphthalene, nitrogen mustard, opioid, oxazole, paclitaxel, phenothiazine, phenylalkamine, phenylpiperidine, piperazine, piperidine, polycyclic hydrocarbon, pyridine, pyrimidine, pyrrolidine, pyrrolidinone, rauwolfa aalkaloid, retinoid, sulfonylurea, tamoxifen, taxol, taxotere, THP-adriamycin, trastuzumab, triazole, vinblastine, vincristine or vinca alkaloid.

"Side effects" or "toxicity" or "adverse drug reactions" of chemotherapeutic agents are observed in the acute phase of chemotherapy administration and in patients cured of the cancer with subclinical tissue damage. There is a higher recognition of drug-related tissue side effects which may be quite severe, disabling and irreversible. The clinician must be aware of the potential tissue/organ complications of chemotherapeutic agents and where appropriate perform a baseline tissue examination before initiating the therapy.

"Clearance" of drug occurs by perfusion of blood to the organs of extraction. "Extraction" refers to the proportion of drug presented to the organ which is removed irreversibly (excreted) or altered to a different chemical form (metabolism). Clearance (CL) is therefore calculated as the product of the flow of blood through the organ and proportion of the drug extracted by the organ.

Clearance of drug normally occurs from the liver and kidneys and it is assumed that only free and not protein bound, drug is available for clearance. For hepatic clearance, passive diffusion through the lipid core of the hepatocyte membranes, available to lipophilic drugs, is augmented by sinusoidal carrier systems particularly for ionized molecules (anionic and cationic) of molecular weights of above 400. Likewise other transporters on the canalicular face transport drugs or their metabolites into bile. This system has two separate processes, hepatic uptake and billiary excretion. With small sized lipophilic drugs that readily traverse membranes hepatic uptake is not a major factor, but with higher molecular weight compounds (above 500) and those containing considerable H-bonding hepatic uptake can become the key clearance process, even if metabolism occurs subsequent to this.

The present invention provides a method to increase in clearance of the orotate derivatives of the pharmaceutical agent from noncancerous or normal tissues as measured by pharmacological studies at least 25% relative to dosing of the pharmaceutical agent. The invention also provides a method to increase in clearance of the orotate derivatives of the pharmaceutical agent from noncancerous or normal tissues as measured by pharmacokinetic studies of at least 50% relative to dosing of the pharmaceutical agent. The invention further provides a method to increase in clearance of the orotate derivative of the pharmaceutical agent from noncancerous or normal tissues as measured by pharmacological studies of at least 100% relative to dosing of the pharmaceutical agent.

The present invention provides a composition that increases clearance of the orotate derivative of the pharmaceutical agent from noncancerous or normal tissues as measured by pharmacological studies of at least 50% relative to dosing of the pharmaceutical agent. It also provides a composition that increases in clearance of the orotate salt of the pharmaceutical agent from noncancerous or normal tissues as measured by pharmacokinetic studies of at least 100% relative to dosing of the pharmaceutical agent. It further provides said composition that increases in clearance of the orotate derivative of the pharmaceutical agent from noncancerous or normal as measured by pharmacokinetic studies of at least 100% relative to dosing of the pharmaceutical agent.

Absorption or efflux occurs by one of three methods, either passive diffusion, active transport or facilitated active transport. Passive diffusion is simply the passage of molecules across the mucosal barrier until the concentration of molecules reaches osmotic balance on both sides of the membrane. In active transport the molecule is actively pumped across the mucosa. In facilitated transport, a carrier generally a protein, is required to convey the molecule across the membrane for absorption.

"Bioavailability" of a drug following oral dosing is the extent to which or rate at which the active moiety of the drug or metabolite enters systemic circulation, thereby gaining access to the site of action. The physiochemical properties of a drug govern its absorptive potential, but the properties of the dosage form which partly depend on its design and manufacture, can largely determine drug bioavailability. Differences in bioavailability among formulations of a given drug can have clinical significance. The concept of equivalence among drug products is important in making clinical decisions.

"Chemical equivalence" refers to drug products that contain the same compound in the same amount and that meet current official standards. However, inactive ingredients in drug products may differ.

"Bioequivalence" refers to chemical equivalents that, when administered to the same person in the same dosage regimen, result in equivalent concentrations of drug in blood and tissues.

"Therapeutic equivalence" refers to drug products that, when administered to the same person in the same dosage regimen, provide essentially the same therapeutic effect or toxicity. Bioequivalent products are expected to be therapeutically equivalent. Sometimes therapeutic equivalence may be achieved despite differences in bioavailability, for example when the therapeutic index is wide (ratio of maximum tolerated dose to the minimum effective dose).

"Absorption" rate is important because even when a drug is absorbed completely, it may be absorbed too slowly to produce a therapeutic blood level quickly enough or so rapidly that toxicity results from high drug concentrations given to achieve the therapeutic level after each dose.

Figure 2:
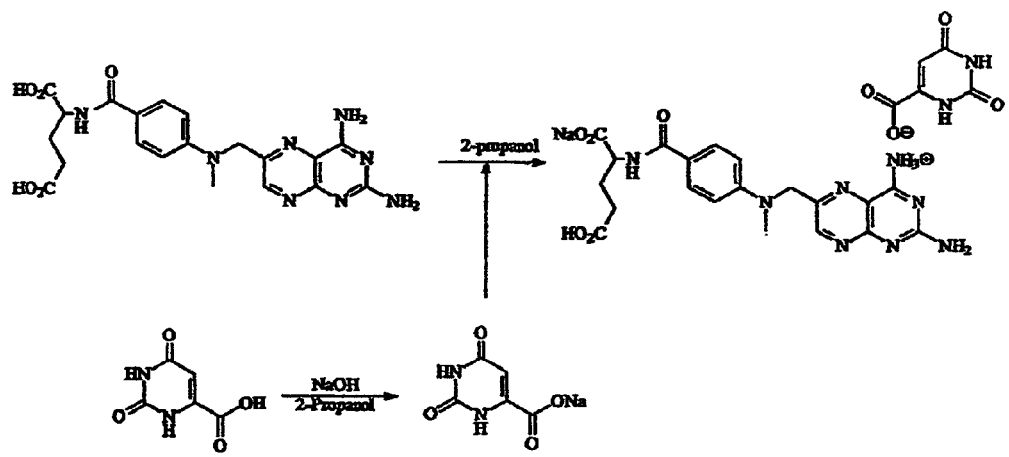
FIG. 2 illustrates the synthesis of methotrexate orotate

"Clearance" of drug occurs by perfusion of blood to the organs of extraction. "Extraction" refers to the proportion of drug presented to the organ which is removed irreversibly (excreted) or altered to a different chemical form (metabolism). Clearance (CL) is therefore calculated as the product of the flow of blood through the organ and proportion of the drug extracted by the organ. FIG. 2 is a schematic illustrating the interplay of hepatic and renal clearance.

Clearance of drug normally occurs from the liver and kidneys and it is assumed that only free and not protein bound, drug is available for clearance. For hepatic clearance, passive diffusion through the lipid core of the hepatocyte membranes, available to lipophilic drugs, is augmented by sinusoidal carrier systems particularly for ionized molecules (anionic and cationic) of molecular weights of above 400. Likewise other transporters on the canalicular face transport drugs or their metabolites into bile. This system has two separate processes, hepatic uptake and billiary excretion. With small sized lipophilic drugs that readily traverse membranes hepatic uptake is not a major factor, but with higher molecular weight compounds (above 500) and those containing considerable H-bonding hepatic uptake can become the key clearance process, even if metabolism occurs subsequent to this.

The present invention provides a method to increase in clearance of the orotate salt of the methotrexate as measured by pharmacokinetic studies at least 25% relative to dosing of the pharmaceutical agent. The invention also provides a method to increase in clearance of the orotate salt of the methotrexate as measured by pharmacokinetic studies of at least 50% relative to dosing of the pharmaceutical agent. The invention further provides a method to increase in clearance of the orotate salt of methotrexate as measured by pharmacokinetic studies of at least 100% relative to dosing of the pharmaceutical agent.

The present invention provides a composition that increases clearance of the orotate salt of the methotrexate as measured by pharmacokinetic studies in of at least 50% relative to dosing of the pharmaceutical agent. It also provides a composition that increases in clearance of the orotate salt of methotrexate as measured by pharmacokinetic studies of at least 100% relative to dosing of the pharmaceutical agent. It further provides said composition that increases in clearance of the orotate salt of the pharmaceutical agent as measured by pharmacokinetic studies of at least 200% relative to dosing of the pharmaceutical agent.

Causes of Low Bioavailability

When a drug rapidly dissolves and readily crosses the intestinal membranes, absorption tends to be complete, but absorption of orally administered drugs is not always complete. Before reaching the vena cava, a drug must move down the gastrointestinal tract and pass through the gut wall and liver, common sites of drug metabolism. Thus a drug may be metabolized during first-pass metabolism before it can be measured in the systemic circulation. Many drugs have low oral bioavailability because of expensive first-pass metabolism.

Low bioavailability is most common with oral dosage forms of poorly water-soluble, slowly absorbed drugs. More factors can affect bioavailability when absorption is slow or incomplete than when it is rapid and complete. That is, slow or incomplete absorption leads to variable therapeutic responses. Slow absorption in the gastrointestinal tract also leads to increased acute and delayed-phase chemotherapy induced nausea and vomiting.

Insufficient time in the gastrointestinal tract is a common cause of low bioavailability. Ingested drug is exposed to the entire gastrointestinal tract for no more than one to two days and to the small intestine for only 2 to 4 hours. If the drug does not dissolve readily or cannot penetrate the epithelial membrane (e.g., if it is highly ionized and polar), time at the absorption site may be insufficient. In such cases, bioavailability tends to be highly variable as well as low. Age, sex, activity, genetic phenotype, stress, disease or previous gastrointestinal surgery can affect drug bioavailability.

Reactions that compete with absorption can reduce bioavailability. They include complex formation, hydrolysis by gastric acid or digestive enzymes, conjugation in the gut wall, absorption of other drugs and metabolism by luminal micro flora.

Assessment of bioavailability from plasma concentration-time data usually involves determining maximum peak concentration, the time at which maximum peak plasma drug concentration occurs, and the area under the plasma concentration time curve (AUC). The plasma drug concentration increases with the extent of absorption. The peak is reached when the drug elimination rate equals absorption rate. AUC is the most reliable measure of bioavailability. It is directly proportional to the total amount of unchanged drug that reaches the systemic circulation.

Drug products may be considered bioequivalent in extent and rate of absorption if their plasma level curves are essentially super imposable. Drug products that have similar AUCs but differently shaped plasma level curves are equivalent in extent but differ in their absorption rate-time profiles.

Absorption occurs by one of three methods, either passive diffusion, active transport or facilitated active transport. Passive diffusion is simply the passage of molecules across the mucosal barrier until the concentration of molecules reaches osmotic balance on both sides of the membrane. In active transport the molecule is actively pumped across the mucosa. In facilitated transport, a carrier generally a protein, is required to convey the molecule across the membrane for absorption.

Methotrexate

Methotrexate is known by its generic name methotrexate, NSC-740 and by its commercial names: MEXATE, FOLEX, RHEUMATREX. It is available in tablet, powder and solution forms. Methotrexate sodium tablets contain 2.5 mg methotrexate in bottles of 100. Methotrexate sodium for injection, freeze dried preservative free is available in 20 mg, 50 mg and 1 g vials in powder form. It can be reconstituted with any sterile preservative free fluid such as water or 0.9% saline. Methotrexate sodium for injection, preservative protected is available at 25 mg per mL in 2 mL (50 mg) and 10 mL (250 mg) vials.

The present invention provides equivalent doses of methotrexate sodium in the form of orotate for each of the formulations and further dosages as necessary. Methotrexate orotate may be administered via oral, intravenous, intraarterial, or intrathecal administration.

Methods of Reducing Side Effects of an Agent by Converting it to an Orotate Derivative.

At conventional concentrations, methotrexate enters cells by facilitated transport via the folate transporter. At higher concentrations, it enters cells via passive diffusion. Oral absorption of methotrexate is rapid but poor and unpredictable and tends to decrease with increasing doses and in the presence of food. Methotrexate distributes widely in body tissue and is approximately 50% bound to plasma protens. Elimination of methotrexate from plasma has been shown to be age and dose dependent, with a half life of 0.75 to 2.0 hours and a beta half-life of 3.5 to 10.0 hours, and a gamma half life of 27 hours. Most methotrexate (50% to 80%) is eliminated unchanged in the urine in the first 12 hours. Methotrexate clearance approximates creatinine clearance and as such should be used with caution in patients with renal impairment. Some of the disadvantages and difficulties associate with use of methotrexate have been solved by the present invention by structurally changing the sodium methotrexate to sodium methotrexate orotate.

The present invention describes methotrexate orotate and methods of increasing the oral bioavailability of pharmaceutical agents that are poorly absorbed from the gastrointestinal tract by converting them into orotate salts. The invention describes an increased clearance of methotrexate when given as an orotate derivative, compared with the pharmaceutical form of the drug, thus reducing the potential for toxicity of methotrexate at the time of drug administration and in the long term after the primary cancer or the disease is cured. Therefore, an especially useful formulation of the orotate derivative of the pharmaceutical agent can provide rapid onset and consistent action using a lower dose and reduce drug interactions and side-effects. All cited references are incorporated herein fully.

Orotic acid, a free pyrimidine is important in the synthesis of uridylate (UPP) a major pyrimidine nucleotide. Pyrimidines play a central role in cellular regulation and metabolism. They are substrates for DNA/RNA biosynthesis, regulators of the biosynthesis of some amino acids, and cofactors in the biosynthesis of phospholipids, glycolipids, sugars and polysaccharides. The classical de novo pyrimidine biosynthetic pathway ends with the sysnthesis of UMP. Biochemistry, ed Lubert Stryer, ed, W. H. Freeman & Co NY, $4^{th}$ ed, 739-762 (1995). It has also been reported that 5-Fluorouracil is toxic to the liver, as measured by incorporation in the acid soluble fraction, RNA and DNA in normal tissues in the liver of rats. Orotic acid administration decreased the incorporation into the liver and intestinal RNA, thus suggesting that it reduces 5-FU induced toxicity in the liver. El Hag IA et al, In vivo 1: 309-312 (1987). The present invention provides drug orotate derivatives that under go dissolution to release the drug as a charged molecule and free orotic acid, which in turn reduces drug-induced liver, heart or other tissue toxicity.

The invention provides methods and compositions to increase effectiveness of the orotate derivative of the pharmaceutical agent as measured by improvement in bioavailability and clearance of methotrexate where the drug is known to cause toxicity or has the potential to induce toxicity in the long term because of tissue accumulation of the drug.

6. EXAMPLES

Example 1

Chemical Synthesis of Sodium Methotrexate Orotate

FIG. 2 illustrates the synthesis of Sodium Methotrexate Orotate. Orotic acid (1.74 g) was treated with sodium hydroxide (0.45 g) in water (100 mL). The mixture was warmed, stirred for 1 h and stored in the refrigerator overnight. Etanol (30 mL) was added to the solution and the precipitate was collected by filtration to give sodium orotate as a colorless solid which was dried in vacuum over night and used for the next step (1.51 g).

Sodium orotate made in above step (0.43 G) and methotrexate (1.000 g, 1 eq) were suspended in water (60 mL) and stirred for 4 h at 50° C. in an atmosphere of argon. The solution was cooled in a refrigerator overnight, and the precipitate was collected by filtration. The solid was dried in vacuum for 24 hr to give the sodium methotrexate orotate as a colorless solid (J-1220-10-I, 1.27 g). Mass Spectroscopy (FIG. 3) and Nuclear Magnetic Resonance (FIG. 4) indicate that the structure is sodium methotrexate orotate.

Example 2

Response of SC DU-145 Prostate Tumor to Treatment with Methotrexate and Methotrexate Orotate The purpose of the experiment was to evaluate the antitumor efficacy of methotrexate (MTX) and its orotate derivative (MTX orotate) against subcutaneously (SC) implanted DU=145 human prostate tumor xenografts in male athymic NCr-nu/nu mice.

Drug formulation—2.7 mg/mL solution of MTX (Sigma-Aldrich, catalog no. M9929, lot no. 114K1572 used on days 15 and 19, and catalog no. A6770, lot no. 21H0324 used on days 19, 23 and 35) was formulated fresh on each day of treatment in 2% sodium bicarbonate in water for injection (WFI). The 2.7 mg/mL solution was diluted with sodium bicarbonate in WFI to 1.8 and 1.2 mg/mL.

MTX orotate (lot no J1220-B-I) was synthesized from MTX, lot no. 114K1572, as described in Example 1. A 4.25 mg/mL solution of MTX orotate was formulated fresh on each day of treatment in 2% bicarbonate in WFI to 2.83 and 1.89 mg/mL. Control group was treated with 2% sodium bicarbonate in WFI. Both compounds and the vehicle were administered to mice by exact individual animal's body weight on each day of treatment with the injection volume being 0.1 mL/10 g of body weight.

Seven groups of 10 mice per group were injected intraperitoneally (ip) once every four days for a total of 3 injections (q4d×3, Days 15, 19, 23 and 35) as follows: Group 1—2% sodium bicarbonate, Groups 2, 3 and 4 with MTX at 27, 18, and 12 mg/kg/dose, respectively. Groups 5, 6, and 7 were treated with MTX orotate at dosages 42.5, 28.3 and 18.9 mg/kg/dose respectively (based on MW of MTX=454.4 and MW of MTX orotate=714.7).

Figure 1:
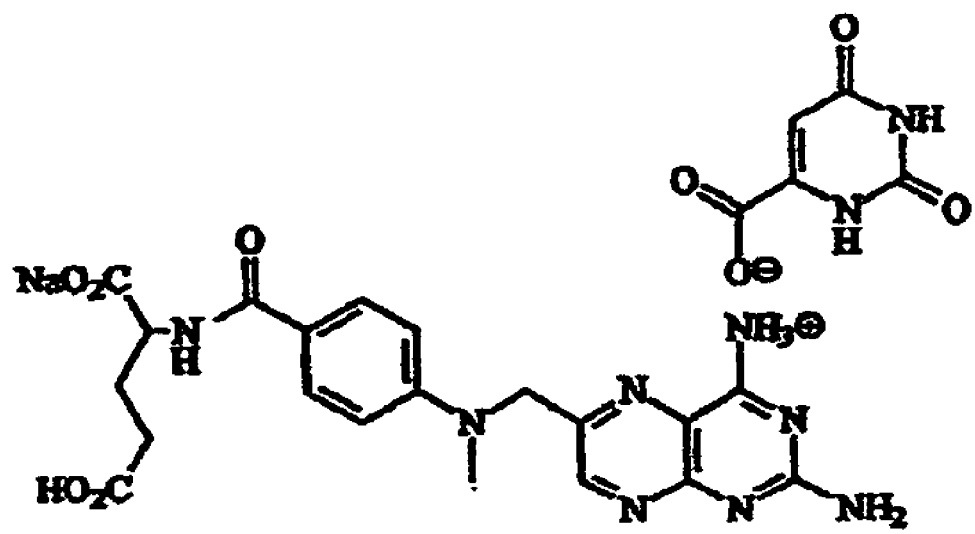
FIG. 1 illustrates the structures of methotrexate orotate

Tumors were measured and volume determined using formula $L×W^2/2=mm^3$; and weight calculated assuming 1 $mm^3=1$ mg. The study was terminated 47 days after tumor implantation Results:

Tumor weight—administration of MTX at dosages of 27, 18, and 12 mg/kg/dose had no effect on tumor inhibition. Administration of MTX orotate at the equivalent dosages of 42.5, 28.3 and 18.9 mg/kg/dose i.p., had no effect at the two low doses but at the highest dose there was a marginal inhibition of the growth of DU-145 prostate tumor xenografts implanted s.c. in male NCr-nu/nu mice. There was no significant difference in tumor growth from administration of MTX orotate when compare with MTX indicating that i.p. administration of MTX orotate. However the highest dose of MTX orotate showed a marginal advantage over MTX (FIG. 1).

Example 3

Pharmacokinetic Analysis of Methotrexate and Methotrexate Orotate

A PK study was done in rats to determine the PK profile and oral bioavailability of methotrexate and compared this to the orotate salt of methotrexate. This was done in male Spagrue-Dawley rats. This compound was administered intravenously (IV; 10 mg/kg; for methotrexate and 15.7 mg/kg for methotrexate orotate 1 mL/kg; vehicle 1% $NaHCO_3$ in 0.9% saline) or via oral gavage (PO; 100 mg/kg methotrexate; 157 mg/kg methotrexate orotate; vehicle 1% $NaHCO_3$ in 0.9% saline) and the plasma levels of compound in the plasma were determined at specified times. By calculating the ratio of the area under the curve for the compound concentrations (estimated for infinity as is typically done) for PO vs IV, percent oral bioavailability can be determined. Of course normalization for the different doses given IV vs PO was taken into account for determination of oral bioavailability.

Results

The PK profiles for methotrexate and methotrexate orotate for IV and PO treatment are summarized in Tables 1 and 2.

The IV PK profile for methotrexate and methotrexate salt were fairly similar with nearly identical elimination half-lifes. Methotrexate orotate did have a higher apparent volume of distribution and plasma clearance rate, giving it a slightly lower area under the curve (AUC). When given orally, methotrexate at the high dose given (100 mg/kg) showed poor (6%) oral bioavailability and showed multiple peaks and troughs consistent with multiple modes of disposition (Goodman and Gilman, The Pharmacological Basis of Therapeutics, Ed 10, 2001). Methotrexate remained in the plasma for a prolonged period with a highly variable elimination half-life. Methotrexate orotate had twice the oral bioavailability of methotrexate.

Methotrexate orotate appeared to get into the plasma somewhat slower than methotrexate, but its elimination half-life was shorter. Overall, its oral PK profile was fairly similar to methotrexate.

TABLE 1

| Treatment | Elim Half-Life (hr) | Cmax ng/mL plasma | Tmax (hr) | Vd (mL/kg) | Cl mL/hr/kg | AUC Ng-hr-mL |
|---|---|---|---|---|---|---|
| Methotrexate IV | 0.44 ± 0.01 | 3780 ± 636 | 0.1 ± 0.0 | 6121 ± 671 | 9432 ± 1039 | 1151 ± 142 |
| Methotrexate PO | 31.4 ± 15.4 | 51 ± 12 | 0.9 ± 0.6 | 6811662 ± 3415946 | 152227 ± 15436 | 671 ± 70 |
| % bioavailability | | | | | | 6% |

TABLE 2

| Treatment | Elim Half-Life (hr) | Cmax ng/mL plasma | Tmax (hr) | Vd (mL/kg) | Cl mL/hr/kg | AUC Ng-hr-mL |
|---|---|---|---|---|---|---|
| Methotrexate Orotate IV | 0.47 ± 0.00 | 2843 ± 121 | 0.1 ± 0.0 | 10804 ± 733 | 15785 ± 1025 | 792 ± 62 |
| Methotrexate Orotate PO | 17.7 ± 8.0 | 59 ± 20 | 1.6 ± 0.4 | 3345180 ± 472947 | 193983 ± 31091 | 1140 ± 390 |
| % bioavailability | | | | | | 14% |

These results indicate that when given orally, methotrexate at the high dose given (100 mg/kg) showed poor oral bioavailability (6%) when compared with methotrexate orotate which showed double the bioavailability (14%). Methotrexate orotate appeared to get into the plasma slower than methotrexate but its elimination half life was shorter than that of methotrexate. Both these observations distinguish methotrexate orotate as an improved derivative of methotrexate.

The present invention is not to be limited in scope by the embodiment disclosed in the example which is intended as an illustration of one aspect of the invention and any methods which are functionally equivalent are within the scope of the invention. Indeed, various modifications of the invention in addition to those shown and described herein will become apparent to those skilled in the art from the foregoing description. Such modifications are intended to fall within the scope of the appended claims.

Those skilled in the art will recognize, or be able to ascertain using no more than routine experimentation, any equivalents to the specific embodiments of the invention described herein. Such equivalents are intended to be encompassed by the claims.

What is claimed is:

1. A compound having the formula:

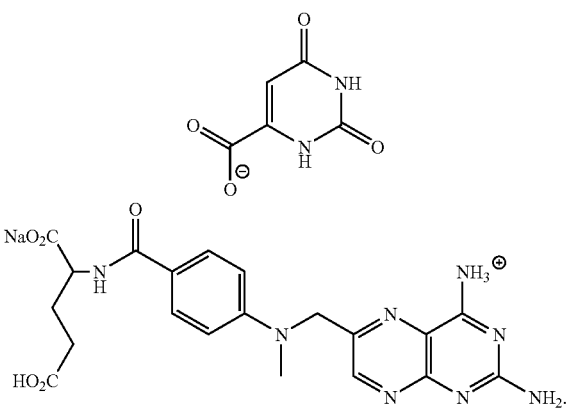

2. A composition comprising methotrexate orotate.

* * * * *